(12) United States Patent
Linkner et al.

(10) Patent No.: US 11,540,976 B2
(45) Date of Patent: Jan. 3, 2023

(54) VIAL ADAPTER FOR DRAWING DRUGS FROM A VIAL

(71) Applicant: Skin NY Dermatology, PLLC, New York, NY (US)

(72) Inventors: Rita V. Linkner, New York, NY (US); Marc-Alan Levine, Pottstown, PA (US)

(73) Assignee: SKIN NY DERMATOLOGY, PLLC, New York, NY (US)

( * ) Notice: Subject to any disclaimer, the term of this patent is extended or adjusted under 35 U.S.C. 154(b) by 300 days.

(21) Appl. No.: 16/798,346

(22) Filed: Feb. 22, 2020

(65) Prior Publication Data

US 2020/0276085 A1    Sep. 3, 2020

Related U.S. Application Data

(60) Provisional application No. 62/812,870, filed on Mar. 1, 2019.

(51) Int. Cl.
    *A61J 1/20* (2006.01)
    *A61K 38/48* (2006.01)

(52) U.S. Cl.
    CPC ............ *A61J 1/2096* (2013.01); *A61J 1/201* (2015.05); *A61J 1/2048* (2015.05); *A61J 1/2079* (2015.05); *A61K 38/4893* (2013.01)

(58) Field of Classification Search
    CPC ......... A61J 1/20; A61J 1/2003; A61J 1/2006; A61J 1/201; A61J 1/2086; A61J 1/2089; A61J 1/2093; A61J 1/2096; A61J 1/2013
    See application file for complete search history.

(56) References Cited

U.S. PATENT DOCUMENTS

| | | | | |
|---|---|---|---|---|
| 5,649,907 | A | * | 7/1997 | Mori .................. A61M 5/1408 604/82 |
| 6,474,375 | B2 | * | 11/2002 | Spero ................ A61J 1/2089 604/416 |
| 2005/0033260 | A1 | * | 2/2005 | Kubo .................. A61J 1/2089 604/411 |
| 2008/0142388 | A1 | | 6/2008 | Whitley et al. |
| 2011/0062703 | A1 | * | 3/2011 | Lopez ................ A61M 39/22 285/129.1 |
| 2011/0106021 | A1 | * | 5/2011 | Ruegg ................ A45D 34/04 604/290 |
| 2011/0160701 | A1 | | 6/2011 | Wyatt et al. |
| 2012/0296307 | A1 | | 11/2012 | Holt et al. |
| 2013/0053815 | A1 | | 2/2013 | Muciented et al. |
| 2015/0068640 | A1 | | 3/2015 | Garfield et al. |
| 2016/0296420 | A1 | * | 10/2016 | Salimnia ............ A61J 1/2089 |

OTHER PUBLICATIONS

Search Report For International Application No. PCT/US20/19381 dated May 18, 2020.

* cited by examiner

*Primary Examiner* — Nicholas J. Weiss
*Assistant Examiner* — Seth Han
(74) *Attorney, Agent, or Firm* — Neil D. Gershon

(57) ABSTRACT

A vial adapter for reconstituting a drug and drawing a drug from a vial. The vial adapter includes a passageway for passage of a diluent into the vial to mix with and reconstitute the drug and a chamber containing the reconstituted drug drawn from the vial. A vacuum is applied through the adapter to draw the reconstituted drug from the vial. The reconstituted drug can be accessed in one or two ways, either via a luer locked syringe or via a needled syringe.

16 Claims, 12 Drawing Sheets

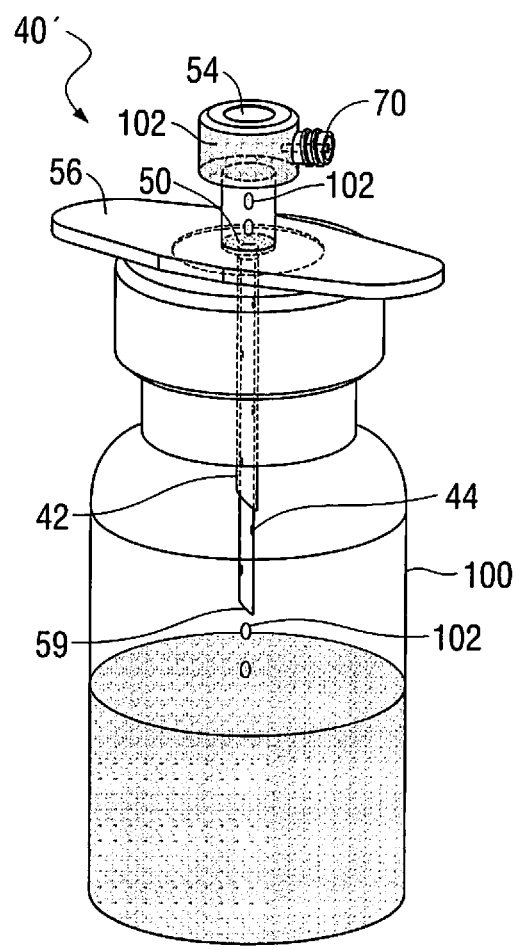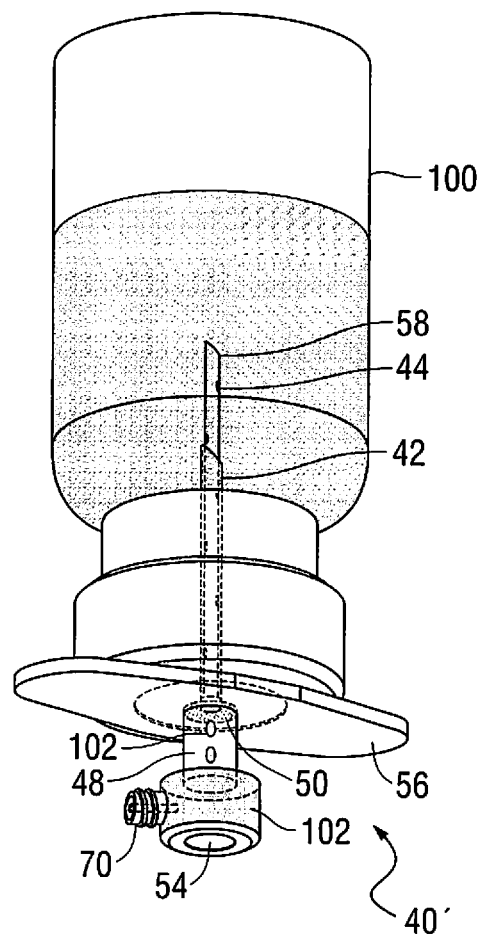
FIG. 6          FIG. 7

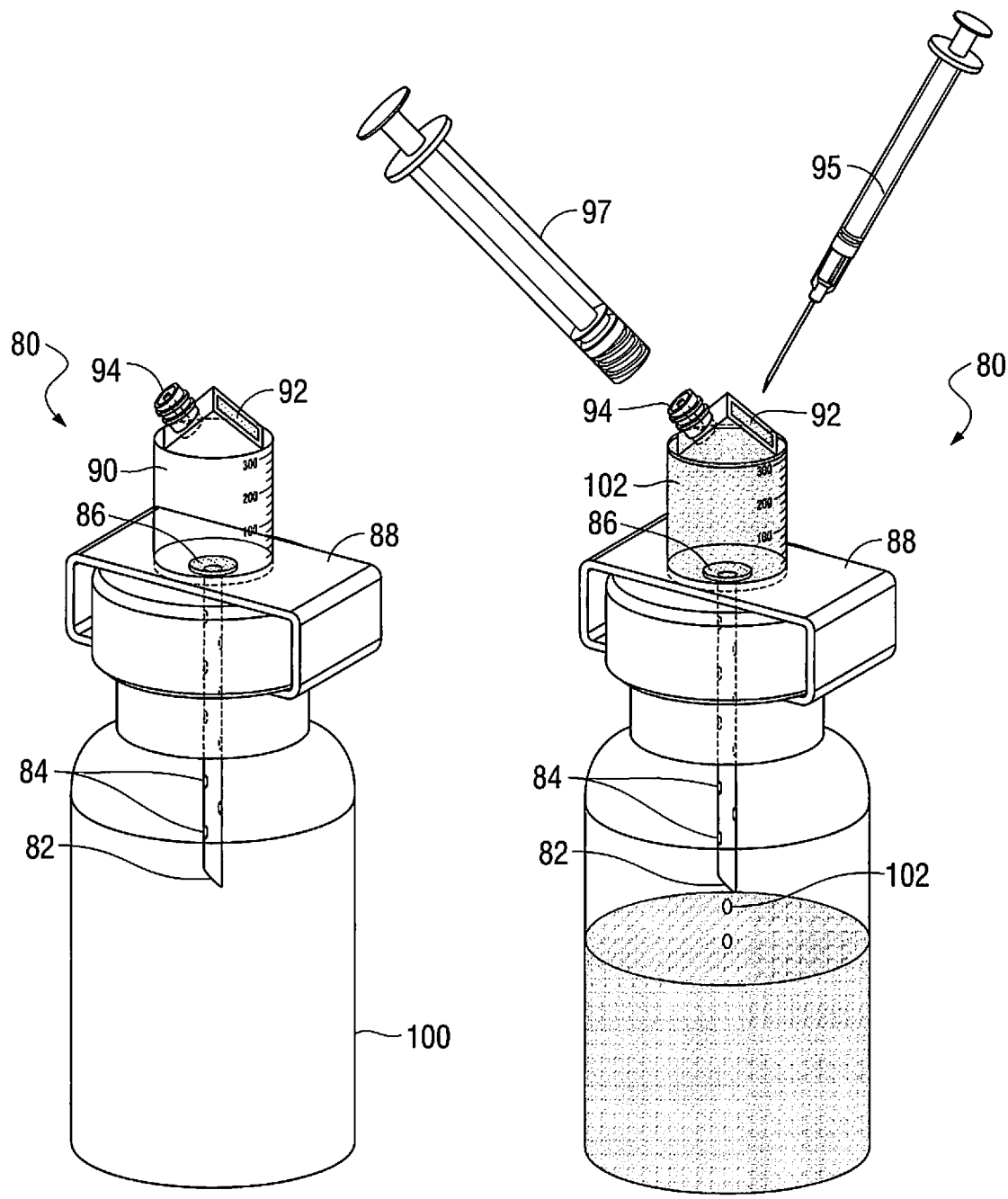
FIG. 8 FIG. 9

VIAL ADAPTER FOR DRAWING DRUGS FROM A VIAL

This application claims priority from provisional application Ser. No. 62/812,870, filed Mar. 1, 2019, the entire contents of which are incorporated herein by reference.

BACKGROUND

Technical Field

This application relates to a vial adapter for cosmetics and other injectables, and, more particularly, to a vial adapter for drawing a drug from a vial.

Background of Related Art

Botulinum toxin is a neurotoxin made from a toxin produced by the bacterium *Clostridium botulinum*. Doctors use this drug in small doses in cosmetics for temporary smoothing of facial wrinkles and improving appearance as it causes relaxation of muscles resulting in smoothing of the overlying skin. Common types of botulinum toxin used for cosmetics are Botox (sold by Allergan, Dysport/Azzalure and Xeomin.

Currently, reconstitution of neurotoxins has to be performed before injection. FDA approved neurotoxins on the market are freeze dried (Dysport) or vacuum dried (Botox), and thus saline needs to be added to the neurotoxin vial. The process of reconstitution and drawing up neurotoxin is currently delegated—dermatologists have medical assistants assigned to this process. If the assistants are not trained properly on reconstitution, there can be inconsistency of results (due to improper mixing) leading to patient complaints of the longevity of treatment. Additionally, if the assistants are not trained properly on drawing up toxin from the vial after reconstitution, there can be a significant loss in revenue due to the expense of this medication. In fact, in some cases, hundreds of dollars of toxin can be left over in the vials if the toxin is not properly drawn. Moreover, many providers will uncap toxin vials to access the remaining toxin solution in the vial to avoid any of the expensive drug being left behind and wasted. This affects the sterility of the contents and the possibility of pieces of the rubber stopper entering this toxin/saline solution and being drawn back into the injecting syringe.

Thus, the current methodologies of reconstitution and subsequent injection of botulinum toxin (or other neuromodulators) are inconsistent and inefficient. Prolonged amounts of time required, loss of byproduct within the vial, and issues with sterility are just a few of the drawbacks of the current methods.

Therefore, the need exists for an improved device and method for reconstitution and drawing of neurotoxin to address the drawbacks of the current devices and methods. Such improved devices and methods could also be utilized for other injectables suffering similar drawbacks.

SUMMARY OF THE INVENTION

The present invention overcomes the problems and deficiencies of the prior art. The present invention provides vial adapters that remedy the inefficiencies of current methods of drawing up neurotoxin. The vial adapters of the present invention enable easier access to the neurotoxin, maintain proper sterility and minimize waste of the neurotoxin. In some embodiments, the vial adapters of the present invention further produce a superior neuromodulator product that is more efficiently reconstituted, i.e., it speeds up the current practice of reconstitution. Various embodiments of the vial adapters are discussed below.

In accordance with one aspect of the present invention, a vial adapter for reconstituting a drug and drawing a drug from a vial is provided including a passageway for passage of a liquid (diluent) into the vial to mix with and reconstitute the drug and a chamber containing the reconstituted drug drawn from the vial. A vacuum is applied through the adapter to draw the reconstituted drug from the vial.

In some embodiments, the vial adapter includes a first port communicating with the chamber to provide access for a syringe to apply the vacuum to draw the reconstituted drug.

In some embodiments, the chamber stores the reconstituted drug and is accessible to withdraw the reconstituted drug therefrom for injection in a patient.

In some embodiments, the passageway is formed in a needle extending within the adapter, the needle having a penetrating tip with an opening for passage of the liquid into the vial.

In some embodiments, the vial adapter includes a second port in communication with the passageway, the second port receiving a syringe for inserting the liquid through the adapter and into the vial.

In some embodiments, the vial adapter includes a filter blocking access of the particles from the vial into the chamber.

In accordance with another aspect of the present invention, a vial adapter for drawing a drug from a vial is provided, the vial adapter including a needle having a penetrating tip for accessing an internal chamber of the vial containing the drug and a chamber proximal of the penetrating tip, the chamber providing access for an injection needle to withdraw the drug. A filter separates the chamber to prevent particles from the vial entering into the chamber through the filter.

In some embodiments, the chamber provides a space for mixing of a diluent with the drug from the vial to reconstitute the drug within the chamber.

In some embodiments, the needle forms a vacuum for drawing the drug into the chamber.

In some embodiments, the chamber includes one or both of a) a membrane penetrable by an injection syringe; and b) an access port for an injection needle.

In accordance with another aspect of the present invention, a method for reconstituting a drug for subsequent injection into a patient is provided. The method comprising the steps of a) inserting a penetrating tip of a needle of a vial adapter into a vial containing a drug, the vial adapter connected to the vial; b) passing a diluent through a passageway in the adapter for entry into the vial to mix with and reconstitute the drug; and c) drawing the reconstituted drug from the vial into a chamber of the adapter.

In some embodiments, the reconstituted drug is drawn from the chamber for injection of the drug into a patient by an injection device.

In some embodiments, the diluent is passed through a passageway in the needle.

In some embodiments, the step of drawing the reconstituted drug from the vial includes applying a vacuum through the vial adapter. In some embodiments, the step of applying a vacuum applies a vacuum through the passageway in the vial adapter. The passageway in some embodiments can be through the needle.

BRIEF DESCRIPTION OF THE DRAWINGS

Preferred embodiment(s) of the present disclosure are described herein with reference to the drawings wherein:

FIG. 6 is a perspective view showing saline in the collection chamber of the adapter of FIG. 5B and flowing into the neurotoxin vial:

FIG. 7 is a perspective view showing the vial adapter of FIG. 6 inverted and the saline and neurotoxin solution collected in the collection chamber of the vial adapter;

FIG. 8 is a perspective view of an alternate embodiment of the vial adapter of the present invention shown attached to the neurotoxin vial of FIG. 5A;

FIG. 9 is a perspective view similar to FIG. 8 showing two different devices which can be inserted into the chamber of the vial adapter to load the collection chamber with saline;

DESCRIPTION OF PREFERRED EMBODIMENTS

Botulinum toxin is a neurotoxin used in small doses in cosmetics for temporary smoothing of facial wrinkles and improving appearance as it causes relaxation of muscles resulting in smoothing of the overlying skin. Before use, the botulinum toxin needs to be reconstituted by the addition of saline. After reconstitution, the toxin is drawn up from the vial for injection into the patient. Proper mixing of the saline with the toxin is required to achieve desired results. Also, due to the expense of the toxin, leaving toxin behind in the vial adds unnecessary expense. Additionally, in trying to retrieve all the toxin from the vial, sterility should be maintained for patient safety.

The present invention provides a vial adapter that enables easier access to the neurotoxin in a vial, maintains proper sterility and minimizes waste of the neurotoxin.

In some embodiments, the vial adapters of the present invention further produce a superior neuromodulator product that is more efficiently reconstituted, i.e., it speeds up reconstitution and improves the consistency of the saline toxin solution.

Various embodiments of the vial adapter of the present invention are discussed below. Before discussing the vial adapters of the present invention, the steps in the current process of reconstitution and drawing up neurotoxin will first be discussed. Note the current process is typically performed by medical assistants, and is tedious and inefficient as well as results in inconsistency, prolonged treatment and added expense.

Figure 1:
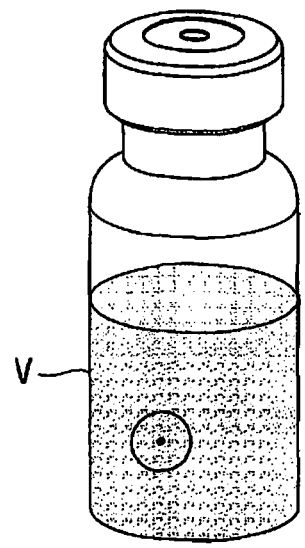
FIG. 1 is a perspective view of a Dysport 300u vial (bottle) of the prior art, the circle highlighting a cored piece of rubber that could potentially be drawn into an injecting syringe.

The steps currently required for drawing up neurotoxin are as follows:

1) Use an 18 g needled-syringe with bacteriostatic saline to reconstitute toxin with desired dilution amount.
2) Switch to a 29 g or smaller needled syringe to draw up desired units of toxin from the vial for injection into the patient (FIG. 1 shows a standard vial designated by letter V).
3) When the reconstituted vial comes to a low solution amount, decap the vial's metallic cap with a bottle opener to permit a needled-syringe access to the remainder of toxin.
4) Use a needled syringe to scrape the bottom of the vial to draw whatever toxin is left in the vial.
5) The remaining solution is then added to a newly reconstituted Toxin vial.

There are several disadvantages associated with each of the foregoing five steps of this process which are noted below, with the numbered list 1-5 below corresponding to the process steps 1-5 above:

1) The 18 g needled-syringe for reconstitution is discarded, adding medical waste.
2) The needle (≤29 g) for drawing up toxin will easily dull by having to penetrate through the thick rubber stopper on the vial, such dulling causing discomfort for the patient during injections and increasing the tendency for bruising.
3) Small cored bits of the rubber stopper can enter the solution that could be drawn into the injecting needled-syringe. This creates the potential for intravascular injection of rubber stopper pieces which can cause infection if injected into the skin or vascular system. Further, due to capillary action on the toxin vial, this step is tedious. The vial must be, tipped to allow remaining toxin to collect in order to be drawn up, and somewhere about 5% to about 8% of the toxin remains in the vial which adds to expense since it could represent as much as a $50 loss per vial if this step is not done correctly.
4) The needle syringe used to scrape the bottom of the vial to draw whatever toxin is left is discarded, resulting in medical waste.
5) If the remaining solution is added to a newly reconstituted toxin vial, the solution has technically been contaminated and is being added to another single-use vial, resulting in non-sterility.

The present invention provides a device and method to overcome the foregoing drawbacks. The present invention provides a vial adapter which is attachable (connectable) to a vial containing the neurotoxin. Note that although the vial adapters described herein are used for cosmetic injectables, such as a neuromodulator, like botulinum toxin types A or B. such as Dysport or Botox, it should be appreciated that other injectables are also contemplated for use with the adapters of the present invention, such as deoxycholic acid, polidocanol, poly-L lactic acid solution, and kenalog by way of example. The vial adapter of the present invention is attached by the user to the medicine (drug) vial.

In some embodiments the vial adapter is dual vented to enable dilution of toxin in its chamber. In some embodiments, it uses pressure differentials to vacuum all the toxin from the vial into the collecting chamber of the adapter, permitting the user to draw up the toxin directly into the needled syringe for injection. In other embodiments, the vial adapter is dual vented and facilitates dilution of toxin in the vial itself. These various embodiments are discussed in detail below.

The vial adapter can also include in some embodiments a filter to prevent cored pieces from the rubber stopper of the vial from being drawn up. Thus, the filter prevents any microscopic matter, such as small pieces of rubber stopper, which are often cored into the solution upon reconstitution with a large-bore needle, to be safely removed from the neuromodulator. This purifies the solution thereby maintaining the quality of the product prior to it being drawn up and then injected into the skin.

Turning now to the drawings wherein like reference numerals identify similar or like components throughout the several views, several embodiments of the vial adapter of the present invention are illustrated.

With initial reference to FIG. 2, the vial adapter of this embodiment is designated generally by reference numeral 10 and includes a spike or needle 12 with a penetrating tip 16 at the distal end and a collection chamber 18 at the proximal end. The collection chamber 18 is defined within outer wall 19 and can be of various shapes/dimensions, one such configuration shown in FIG. 2. The adapter 10 includes a base or flange 26 for abutment with the top of the vial (bottle) containing the neurotoxin. The needle 12 has a plurality of fenestrations (holes) 14 along a length formed in its outer wall shown in a staggered arrangement. The number of fenestrations 14 can vary and the number of fenestrations shown in FIG. 2 is one example of the number and arrangement of fenestrations as other numbers and/or arrangements (e.g., non-staggered) of fenestrations are also contemplated. FIG. 3 illustrates another embodiment of the needle designated by reference numeral 30, having six fenestrations 32 along its length with three on opposing sides of the circumference of the outer wall and staggered. The needle 30 also has a pointed conical penetrating tip 34 which is a different configuration than the beveled pointed penetrating tip of the needle of FIG. 2.

Turning back to FIG. 2, the piercing needle 12 is configured to pierce the rubber stopper on the drug, e.g., neurotoxin, vial (also referred to herein as the bottle), an example of the vial V shown in FIG. 1. The neurotoxin is contained in the bottle under vacuum. The length and width of the needle 12 can vary, however, preferably it is just long enough to reach through the neck of the drug vial and the gauge wide enough to draw toxin in efficiently. In some embodiments by way of example, the length of the needle is between about 0.5 inch to about 1.0 inch and the gauge is between about 18 g and about 22 g, although other dimensions are also contemplated.

The multiple staggered fenestrations 14 (and 32 in the FIG. 3 embodiment) form a microscopic vent to create venting so that when the vial V is inverted, all the toxin is vacuum drawn into the adapter 10 more easily. That is, the holes 14 create a pressure differential between the vial V and the collection chamber 18 creating a vacuum and preventing leakage of the drug, e.g. neurotoxin. The fenestrated needle 12 thereby acts as a sieve when the vial is inverted and drawing up toxin. (As noted above, the toxin is contained in the bottle under vacuum). The integrated filter 20, positioned at a distal end of the collection chamber 18, adjacent base 26, prevents pieces of the cored rubber stopper of the vial V or other particulates from being drawn up into the collection chamber 18, i.e., prevents particulates from entering the collection chamber 18 when drawing in toxin into the chamber 18. Various types of filters can be utilized. One example which can be used is a 5-25 micron filter. Materials which can be used for the filter include by way of example, nylon, polyester, PVP, etc.

A resealable piercing membrane 24 is positioned within the collection chamber 18, illustratively at a proximal end, extending transversely with respect to a longitudinal axis of adapter 10. The membrane 24 is configured so that an injection needle or needled syringe can be inserted through the membrane 24 to access the chamber 18 where the reconstituted toxin has been pulled into (stored/contained) and pulls to draw up the toxin therefrom for injection into the patient. The membrane 24 is formed so it is sufficiently thin on one hand so as not to dull the needled syringe inserted therethrough, while sufficiently thick on the other hand so that multiple piercings by the needled syringe won't cause any leakage. The membrane 24 can be formed of various materials such as silicone, polyurethane, rubber, elastomer, etc. Note the membrane 24 forms a seal to prevent escape of the toxin from the chamber 18 except through a piercing needle or syringe inserted through the membrane 24.

In alternate embodiments, the vial adapter provides a bi-directional function to enable reconstitution of the neurotoxin and drawing of the neurotoxin into the chamber for subsequent access and injection into the patient. Several approaches to reconstituting the neurotoxin of the vial (bottle) are disclosed: in one approach, saline is contained within a chamber in the vial adapter and the toxin is drawn into the chamber of the vial adapter for mixing; in another approach, the saline is contained within a chamber in the vial adapter and injected into the vial for mixing with the toxin and then drawn into the chamber of the vial adapter. In another approach, the saline is injected through a passage in the vial adapter to mix with the toxin in the vial and then drawn through the vial adapter directly into a syringe or into the chamber of the vial adapter.

FIG. 4 illustrates a vial adapter wherein saline from a collection chamber of the adapter is transferred to the vial (bottle) to dilute (reconstitute) the toxin, and the reconstituted toxin is subsequently transferred to the collection chamber. This is achieved by the internal injection cannula.

More specifically, the vial adapter of FIG. 4 is designated generally by reference numeral 40 and has needle 42 with a lumen 43, a penetrating beveled tip 46 at the distal end and a collection chamber 48 at the proximal end. The collection chamber 48 is defined within outer wall 49 and can be of various shapes/dimensions, one such configuration shown in FIG. 4. The adapter 40 can include a base or flange 56. The needle 42, like needle 12 of FIG. 2, has a plurality of fenestrations 44 along a length formed in its outer wall, shown as staggered by way of example. The number of fenestrations 44 can vary and the arrangement of the fenestrations 44 can vary. Thus, the number of fenestrations shown in FIG. 4 is one example of the number and arrangement of fenestrations as other numbers and/or arrangements of fenestrations are also contemplated.

The piercing needle 42 is configured to pierce the rubber stopper on the medicine, e.g., neurotoxin, vial (bottle), such as the neurotoxin vial of FIG. 1. The length and width of the needle 42 can vary, and can in some embodiments be dimensioned as in needle 12 described above.

The multiple staggered fenestrations 44 form a microscopic vent to create venting so that when the vial V is inverted, all the toxin is vacuum drawn into the adapter 40 more easily, the fenestrations 44 creating a pressure differential between the vial V and the collection chamber 48 creating a vacuum and preventing leakage of the drug, e.g. neurotoxin. Note a vacuum source, e.g., a syringe, can also be applied to create a pressure differential between the vial and adapter 40 (and other adapters disclosed herein, e.g., vial adapter 40'), to draw the reconstituted toxin into the chamber of the adapter. A filter 50, like filter 20, is positioned at a distal end of the collection chamber 48, adjacent base 56, and prevents pieces of the cored rubber stopper of the vial V from being drawn up into the collection chamber 48. Various types of filters and materials can be utilized as in filter 20 described above.

A resealable transversely extending piercing membrane 54, similar to membrane 24, is positioned within the collection chamber 48 at a proximal end so that an injection needle or needled syringe can be inserted through the membrane 54 to access the chamber 48 where the reconstituted toxin is pulled into and pulls to draw up the toxin therefrom for injection into the patient.

Figure 2:
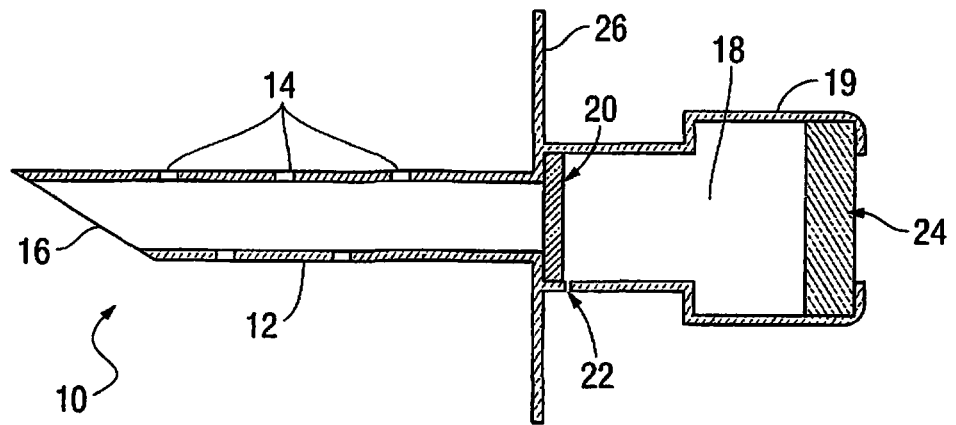
FIG. 2 is a cross-sectional view of one embodiment of the vial adapter of the present invention.
Figure 3:
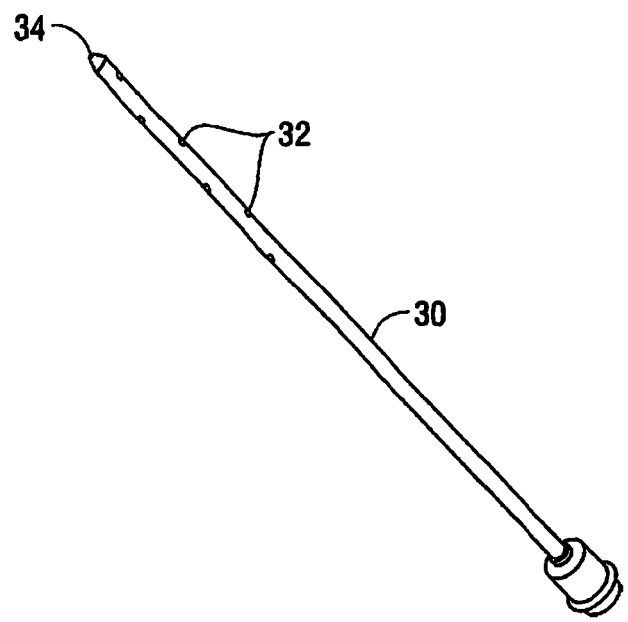
FIG. 3 is a perspective view of an alternate embodiment of the needle of the vial adapter of FIG. 2.
Figure 4:
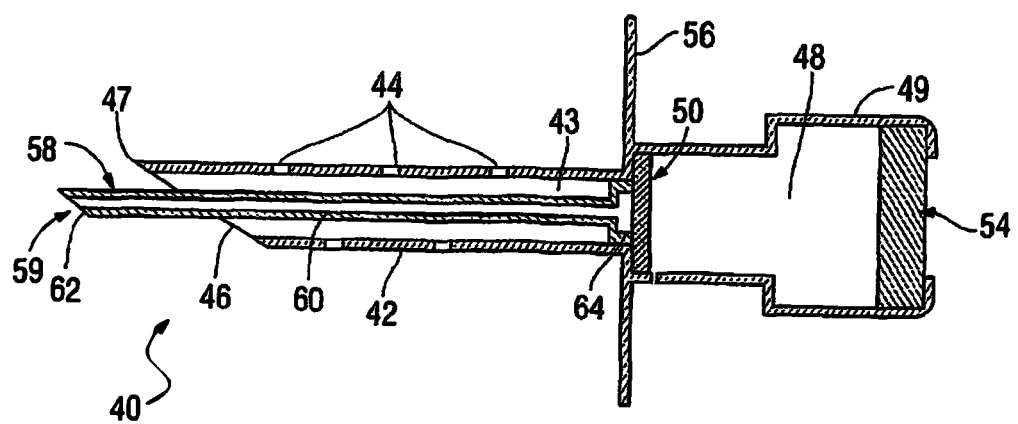
FIG. 4 is a cross-sectional view of an alternate embodiment of the vial adapter of the present invention having a channel for reconstitution.

Vial adapter 40 differs from vial adapter 10 in that it has an injection cannula 58 positioned within the needle 42, illustratively concentric with the needle 42. Cannula 58 is dimensioned to be positioned within the needle 42, preferably concentrically, with a distal tip 62 and opening 59 extending distally of the distal edge 47 of needle 42. Injection cannula 58 includes a lumen 60 and has a suction cannula port 64. Thus, this embodiment differs from the embodiment of FIG. 2 in that saline is transferred from the collection chamber 48 of the adapter 40 into the vial for reconstitution. This difference will be understood in conjunction with the discussion of the method of use below and FIGS. 5-9. Note like vial adapter 10, the reconstituted toxin is transferred (drawn) from the vial to the collection chamber 48. Note the vial adapter 40 can also be used with the side port system of FIG. 14A discussed below.

Note in alternate embodiments, the toxin can be drawn from the vial and reconstituted within the collection chamber containing saline.

Figure 11:
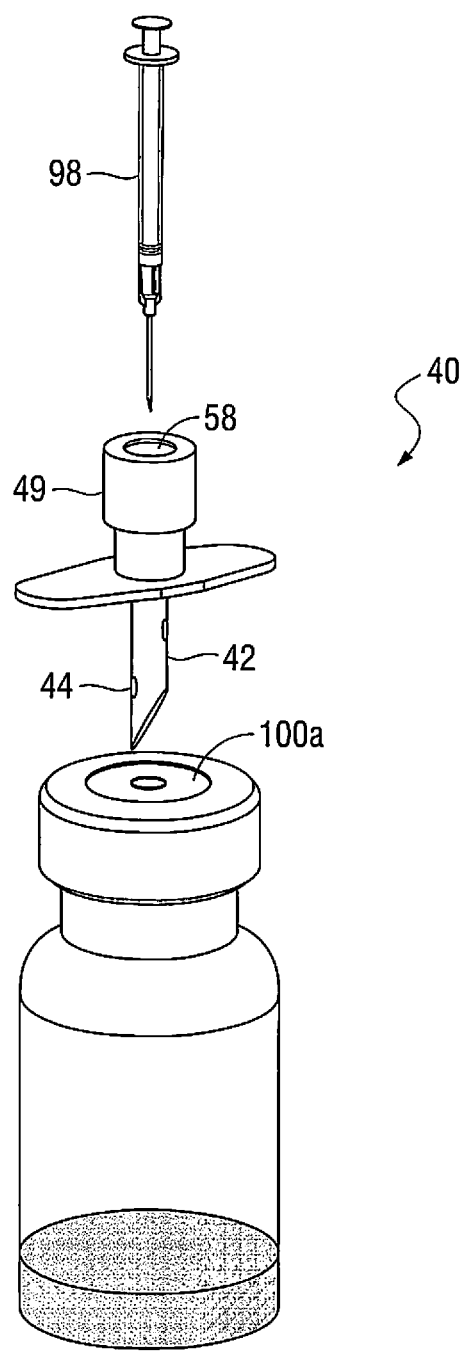
FIG. 11 is a perspective view showing the vial syringe and the vial adapter of FIG. 2 separated.

FIG. 11 illustrates the components for using adapter 40 to draw toxin into the chamber and inject the toxin. The steps for use are as follows: 1) insert the vented needle 42 into the vial stopper 100a of vial 100; 2) inject saline into the collection chamber of the vial adapter by inserting a syringe into the resealable membrane of the vial adapter 40; 3) draw the saline into the vial 100 (via vacuum); and 4) shake the vial 100 to reconstitute. Next, invert the vial 100 (as shown in FIG. 11) and draw toxin into the adapter 40 where it pools in the receiving chamber 48 of adapter 40. Next, draw up reconstituted toxin from the chamber with a needle or injecting syringe 98 to a desired amount for injection into the patient. The vial adapter can during drawing of the toxin be returned to its non-inverted orientation.

Figure 5A:
FIG. 5A is a perspective view of a vial (bottle) of the prior art containing a neurotoxin.
Figure 5B:
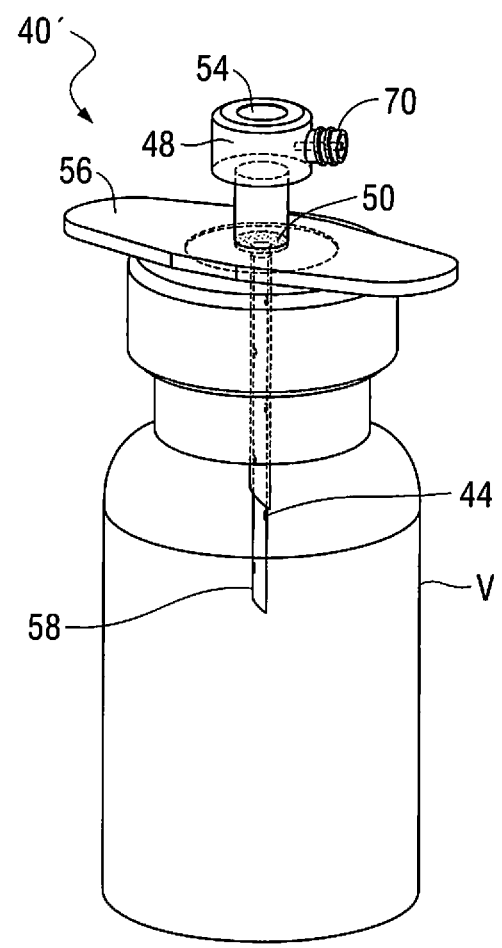
FIG. 5B is a perspective view of an alternate embodiment of the vial adapter of the present invention shown attached to the vial of FIG. 5A.

Turning now to FIGS. 5B-7 these Figures illustrate the use of the vial adapter 40' of the present invention. The vial adapter shown is the vial adapter 40' which is the same as vial adapter 40 except for the luer lock access described below and thus for convenience the same parts have been labeled with the same reference numerals. In FIG. 5B, adapter 40' is shown with base 56 resting on the top (cap) of the vial V to provide a stop for insertion of the needle 42.

The adapter 40', like the other adapters of the present invention disclosed herein, can be either removably or permanently affixed to the vial. If permanently fixed to the vial, it prevents the user from combining the remaining (unused) neurotoxin with another vial of neurotoxin. The collection chamber 48 at this point of attachment to the vial 100 is empty as neither saline for reconstitution nor toxin have been injected or drawn into the chamber 48. As noted above, the saline is pulled from the collection chamber 48 through the needle 42, e.g., a 22 g needle, into the vial V during reconstitution due to the vacuum in the vial. Adapter 40' as shown has two ways to access the collection chamber 48: 1) needled syringe access through the resealable membrane 54 (e.g., a needled syringe from 19 gauge to 32 gauge); or 2) luer lock syringe access through transversely extending luer lock 70 for non-needled access to the chamber (e.g., a luer accessed port for the syringe). Other ways to access through ports or openings in the chamber are also contemplated.

Thus, the user is provided with two options to access the chamber of adapter 40'. The re-sealable membrane can allow fine needles, even a 32 insulin needle gauge, to pierce through without dulling of the injecting needle.

For reconstitution, and with reference to FIG. 6, the collection chamber 48 of the vial 40' is first filled with the desired dilution amount. Note the chamber 48 can be fully filled or partially filled with the dilution fluid (diluent). In one way, this is achieved by insertion of a needled syringe through membrane 54. In another way, this is achieved by insertion of a luer lock syringe through luer lock 70. After filling the collection chamber 48 with the diluent, the needle 42 pierces the rubber stopper of the toxin vial 100 and the dilution liquid is pulled by vacuum of the vial through the needle cannula 58 into the toxin in the vial 100. The fluid, e.g., saline, for reconstitution, is shown schematically in the chamber 48 and vial 100 and designated by reference numeral 102.

Next, to draw up the reconstituted neurotoxin, as shown in FIG. 7, the vial 100 is inverted and the toxin solution bathes the staggered ports/vents 44 allowing the toxin to be pulled into the collection chamber 48. As noted above, the filter 50 prevents particulates from entering the collection chamber when drawing up toxin. After pulling the neurotoxin into the collection chamber 48, the needle 42 is removed from the vial and the neurotoxin in the collection chamber is now ready for withdrawal and injection into a patient.

Figure 10:
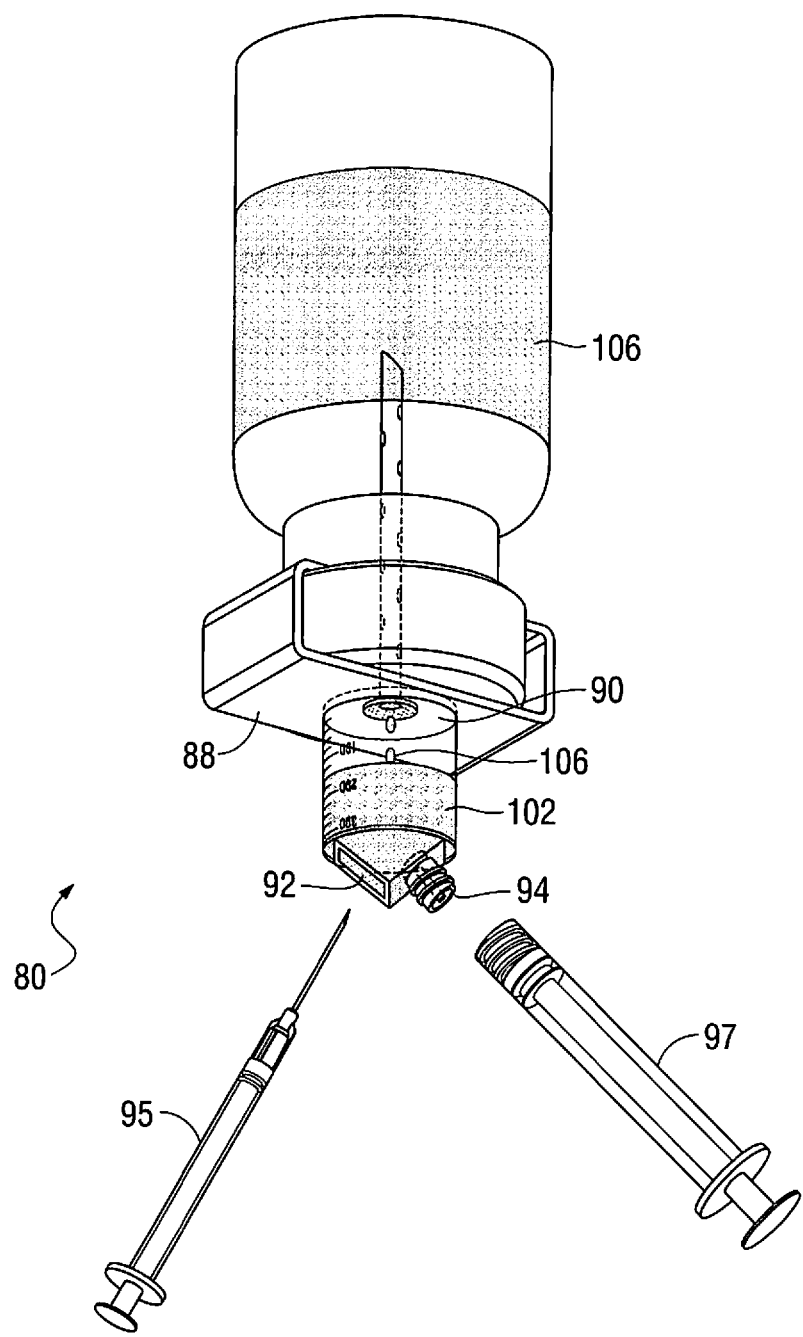
FIG. 10 is a perspective view of the vial adapter of FIG. 9 inverted and the saline and neurotoxin solution collected in the collection chamber of the vial adapter.

FIGS. 8-10 illustrate the method utilizing an alternate embodiment of the vial adapter. Vial adapter 80 has a filter 86 (like filter 50), a fenestrated needle 82 with holes 84 and latch 88 attachable to the cap of the vial. In this embodiment, the latch 88 non-removably latches onto the neck of the vial for one time use. Alternatively it could be removably attached to the vial. Various ways to attach the vial adapter 80 (as well as the other adapters disclosed herein) other than a latch are also contemplated.

The fenestrated needle 82 functions as described above to create a vacuum for drawing up the neurotoxin. Saline is pulled from the collection chamber 90 through the needle 82 into the vial during reconstitution. Collection chamber 90, like chamber 48 of FIG. 5, provides two ways to access the chamber 90: 1) needled access through the resealable membrane 92; or 2) luer lock syringe access through angled luer lock 94 for non-needled access to the chamber 90. The luer lock access 94 can in this embodiment (and in FIG. 5 and the other Figures) be capped. The luer lock access 94 in this embodiment is shown angled with a respect to the longitudinal axis of the adapter but could be positioned at other angles including a 90 degree angle as in the embodiment of FIG. 5. The other luer lock accesses and membrane access of the other embodiments disclosed herein can also be positioned at angles other than those shown.

The collection chamber 90, like chamber 48, provides for loading of saline for reconstitution therein and for withdrawal of reconstituted toxin therefrom. In some embodiments, the chamber 90 can be configured to hold 3 cc of total volume, however, other volumes are also contemplated as are larger or smaller chambers to hold different volumes. The collection chambers of the other vial adapters disclosed herein can also be configured to hold a volume of 3 cc or other volumes.

FIG. 9 illustrates using either a syringe 97 connectable to the luer lock access 94 or a needled syringe 95 penetrating the angled resealable member 92 to load the collection chamber 90 with saline.

As further shown in FIG. 9, once the chamber 90 of the attached vial adapter is fully or partially filled with saline, the vacuum of the vial 100 directly pulls the saline 102 through the needle 82 (e.g., a 22 gauge needle) into the vial to completely reconstitute the toxin. Then, after such reconstitution, as shown in FIG. 10, the vial 100 is inverted and the toxin bathes the staggered ports/vents on the needle 82 allowing toxin to be pulled into the collection chamber 90, with the filter 86 preventing particulates from entering the collection chamber when drawing up toxin. The toxin in the collection chamber 90 can then be drawn out with a luer lock syringe through luer lock 94 or with a needled syringe through the resealable membrane 92.

Thus, as can be appreciated, the two accesses of the vial adapters provide alternatives for the user to inject the saline into the chamber as well as alternatives to withdraw the toxin into the chamber. Note the vial adapters in some embodiments can include only one of the accesses (i.e., either the membrane or luer lock) or other types of accesses.

Figure 12:
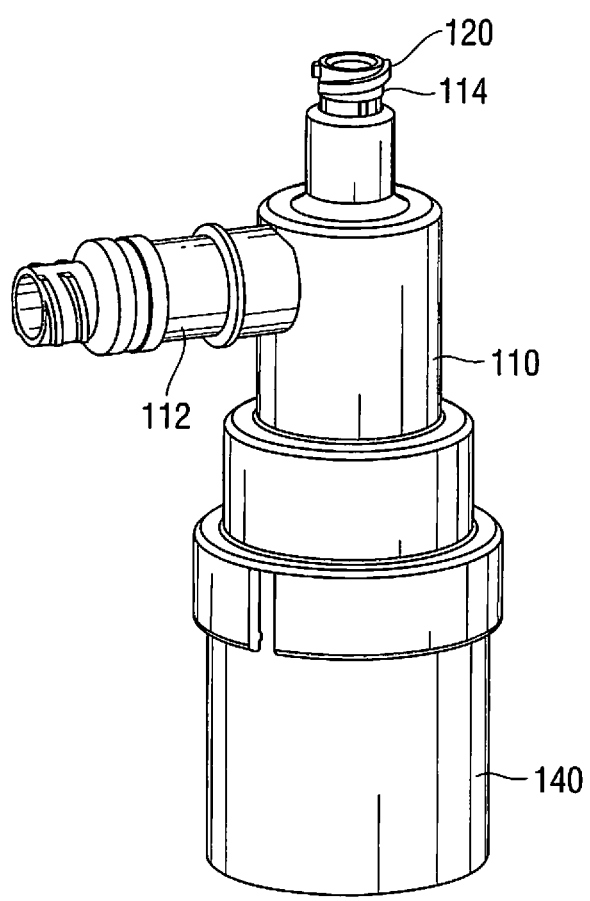
FIG. 12 is a perspective view of an alternate embodiment of the vial adapter of the present invention shown attached to a vial of neurotoxin.
Figure 13:
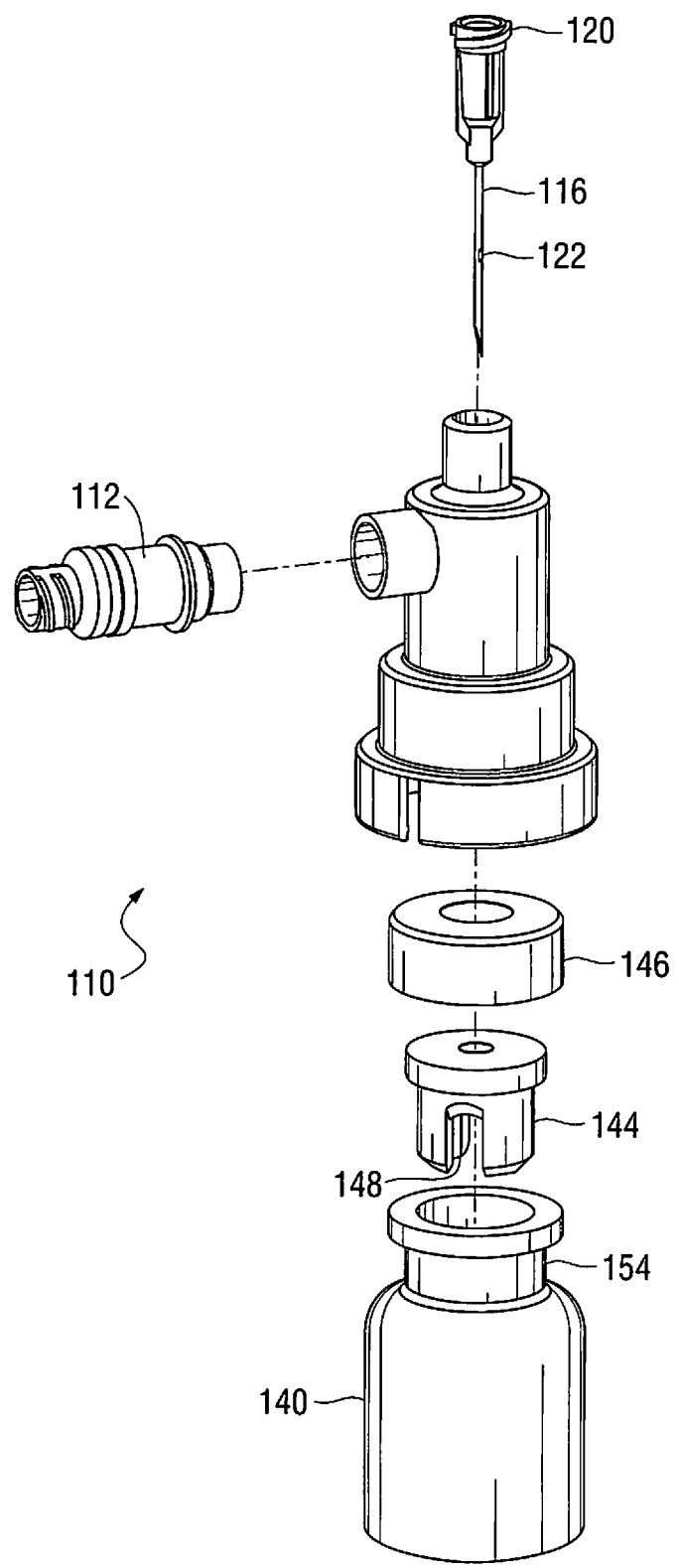
FIG. 13 is an exploded view of the vial adapter of FIG. 12 shown prior to attachment to the neurotoxin vial.

FIGS. 12-14 illustrate an alternative embodiment of the vial adapter of the present invention. The vial adapter 110 provides for passing of a dilution fluid into the drug containing vial to reconstitute the drug and provides for passing the reconstituted drug through the vial adapter for retrieval for injection of the drug into a patient. The reconstituted drug is passed by application of a vacuum.

More specifically, vial adapter 110 has a side port 112 and a top port 114 (as viewed in the orientation of FIG. 12). Extending downwardly from the top port 114 is a needle 116 which forms a channel 119 for passage of dilution fluid such as saline into the vial for reconstitution. Needle 116 can be permanently affixed within adapter 110 such as by bonding, although other methods are also contemplated. The needle 116 can be attached at a proximal portion 117 to an internal proximal wall 113 of the vial adapter 110. A luer lock with external threads 120 is provided at the proximal end of the needle for mounting of a syringe to inject saline for reconstitution. The needle end can be closed at a proximal end to provide a closed system for vacuum or can be closed once the syringe is inserted to provide a closed system. The needle can include a resealable member at a proximal end for insertion of a needle of syringe 162 to inject saline. At the distal end of the needle is a penetrating tip 118 for penetrating into the vial (bottle) 140 of neurotoxin. The vial 140 includes a chamber 142 for holding the neurotoxin, a rubber stopper 144 and a band or ring 146, e.g., a metal ring, circumferentially surrounding the rubber stopper 144 for holding the rubber stopper 144 in the vial 140. Thus, the ring 146 is interposed between the rubber stopper 144 and the internal wall 152 at the neck 154 of the vial 140. The rubber stopper 144 includes a cutaway 148 to allow the stopper 144 to push out against the exterior. The vial 140 can include a peelable tab on its cap that is peeled away to enable access by the needle through the rubber stopper 144.

The needle 116 can further include a filter adjacent the openings, either inside or outside the needle, to prevent unwanted particles, e.g., pieces of the rubber stopper from the vial, entering the chamber 124. Alternatively, or in addition, the openings in the needle can be dimensioned to be small enough so such particles could not pass through the openings. Thus, the filters disclosed herein can prevent micro particles from the diluent in the vial entering into the collection chamber.

The vial adapter 110 further includes a chamber 124 for receiving the diluted neurotoxin, i.e., after reconstitution. The reconstituted drug passes through the needle 116, chamber 124 and side port 112 as described below. The openings 122, 123 in needle 116 communicate with the chamber 124, i.e., open into chamber 124. This communication enables application of the vacuum to the vial and suctioning of the reconstituted drug from the vial. Although two openings are shown, it is contemplated that a different number of openings can be provided. Base 126 forms a floor to close off the bottom of the chamber 124. The chamber 124 is fully enclosed to form a closed system as described below.

Side port 112 is shown transverse to a longitudinal axis of the vial adapter 110 but can alternatively be positioned at other angles. Side port 112 has a luer lock with external threads 130 for mounting of a syringe to withdraw the neurotoxin from the chamber 124. The luer lock has a one way valve normally closed to provide a closed system, and a syringe can be inserted through the valve to access the chamber, e.g., a male part of the syringe can open the valve when the syringe is attached. Various types of valves can be utilized such as a penetrable membrane, leaf valve, etc. Wall 134 provides a stop for the bellows of the luer valve. The luer valve side port is attached to the vial adapter 110 by bonding, overmolding, or other techniques. With the syringe mounted to the luer, channel 115 communicates with the chamber 124. Therefore, the passageway and/or chamber for the vacuum can be considered to include this channel. In other forms of mounting, e.g., extending within the port 112, then the passageway and chamber might be considered to only include the chamber 124. Note the needle provides a passage or channel from the vial into the chamber 124 via its openings 122, 123.

The use of the vial adapter 110 for drawing neurotoxin from the vial 140 will now be described. The vial adapter 110 is attached to the vial 140 either removably or permanently. Vial adapter 110 has a bump or projection 136 at its distal end to grip the vial 140. When attached, the distal penetrating tip of needle 116 penetrates the stopper 144 so that the tip 118 and its opening 118a communicate with internal chamber 142 of vial 140. A closed system is formed due to the base 126, the internal wall and the sealed ports 112, 114. A syringe (e.g., syringe 162 of FIG. 14A) is then attached to the luer of the needle 116 so it is in communication with the channel (passageway) 119 within needle 116. Upon injection of saline from the syringe, the saline flows through passageway 119 exiting opening 118a to enter the chamber 142 of the vial 140 as it is pulled down due to the vacuum of the vial 140. With such vacuum, the saline enters the chamber 142 of the vial 140 and generally does not exit the openings 122, 123 of the needle 116, although in some applications a small amount of saline can enter the chamber 124 of the adapter 110. Note, optionally, initially after the syringe containing saline is attached, a single squirt can be made to ensure flow through the needle 116. The syringe in some embodiments contains 3 cc of saline, but other amounts are also contemplated.

Once the saline has been mixed with the drug within the vial 140, the syringe 160 (FIG. 14B), which is attached to the side port 112 (either before or after attachment of syringe 162 to top port 114), is ready for withdrawal of the reconstituted (diluted) neurotoxin from the vial 140 into the chamber 124 of the vial adapter 110. The vial 140 and vial adapter 110 are inverted (similar to the orientation shown in FIG. 7) and the syringe 160 is retracted to provide a vacuum force greater than the vacuum force of the vial 140 to draw the reconstituted toxin into the chamber 124 of the vial adapter 110. Note the vacuum is applied through side channel 115, chamber 124, through needle openings 122, 123 and needle 116 so the reconstituted toxin enters the distal opening 118a in needle 118 and is drawn through needle passageway 119, out through openings 122, 123, into chamber 124 through channel 115 and into the syringe 160. The syringe 160 in some embodiments has a volume greater than the volume in the vial, and could for example hold 10 cc. After the toxin is drawn from the vial from vial 140, the syringes 160 and 162 can be removed.

Note in some embodiments, all the toxin from the vial 140 is drawn into the syringe 160. The toxin can then be drawn from syringe 160 by another smaller syringe for injection of the toxin into the patient. In some embodiments, the toxin can be held in the chamber 124 instead of in the syringe 162. In such embodiments, a vacuum source other than syringe 160 can be utilized to communicate with passage 119 to suction the toxin into the chamber 124. In such embodiments, the toxin in the chamber 124 could be accessed by insertion of a needle through the side port 112, top port 114 and/or by providing a penetrable membrane as in the embodiment of FIG. 9.

Note the extra volume syringe 160 and application of the vacuum creates a vortex which can provide additional mixing of the toxin and dilution liquid. Also, the suction/vacuum can be intermittently broken to allow passage back into the vial and then back into the chamber/syringe for additional mixing. To provide an intermittent vacuum, retraction of the syringe 160 can be controlled, e.g., released (pulled back and forth). Alternatively, a valve or an openable opening can be provided to selectively open the chamber 124 or allow air in to open the otherwise closed system.

Figure 14A:
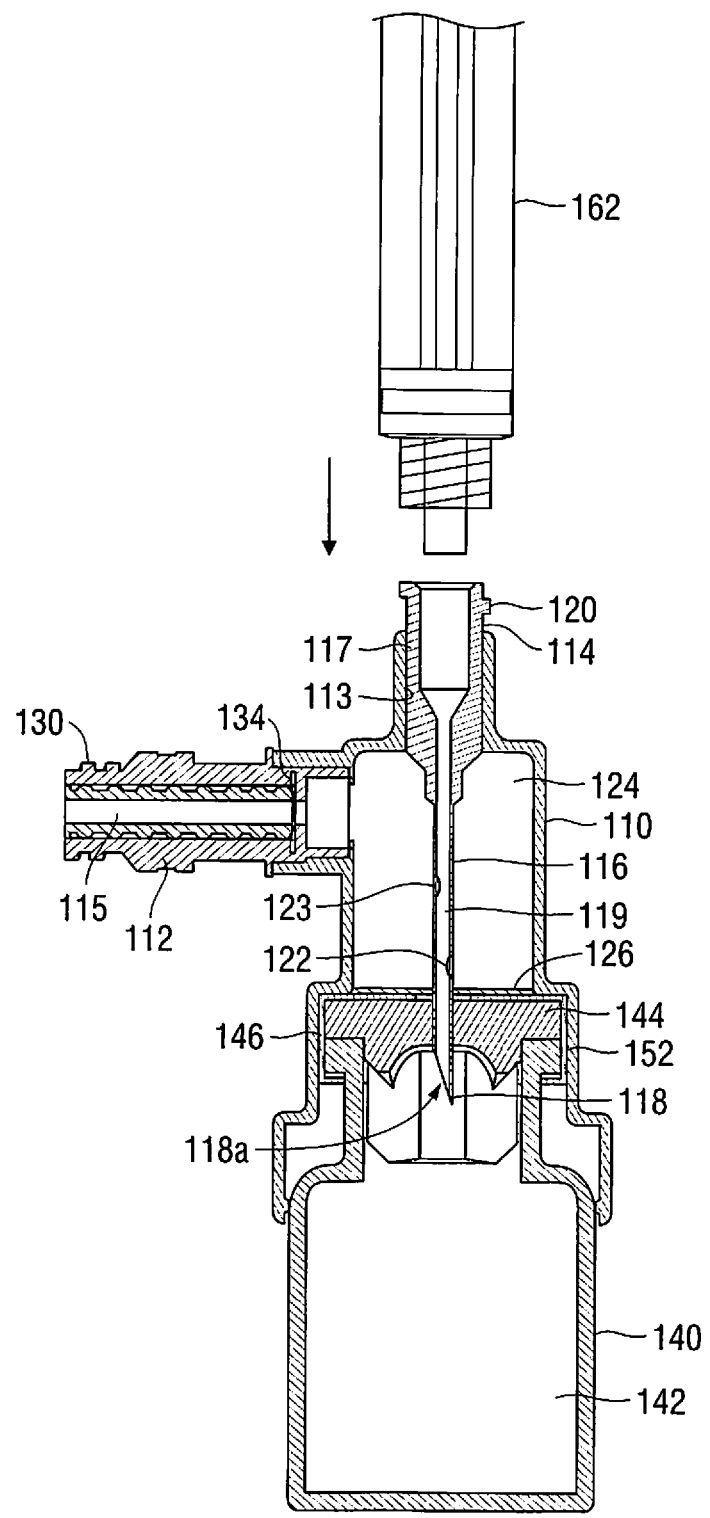
FIG. 14A is a cross-sectional view of the vial adapter attached to a neurotoxin vial of FIG. 13 and further showing a syringe being inserted into a top port of the vial adapter of the present invention.
Figure 14B:
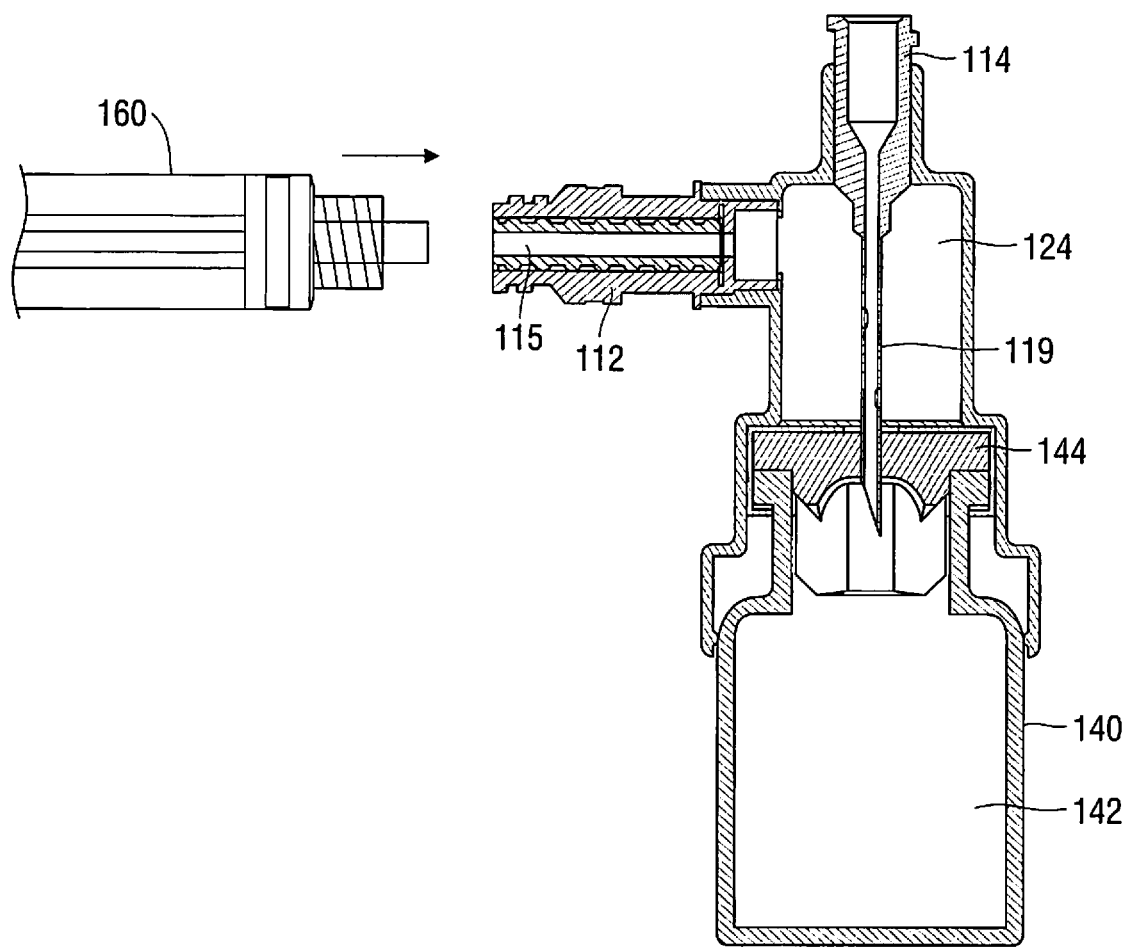
FIG. 14B is a view similar to FIG. 14A showing a syringe being inserted into a side port of the vial adapter.
Figure 15:
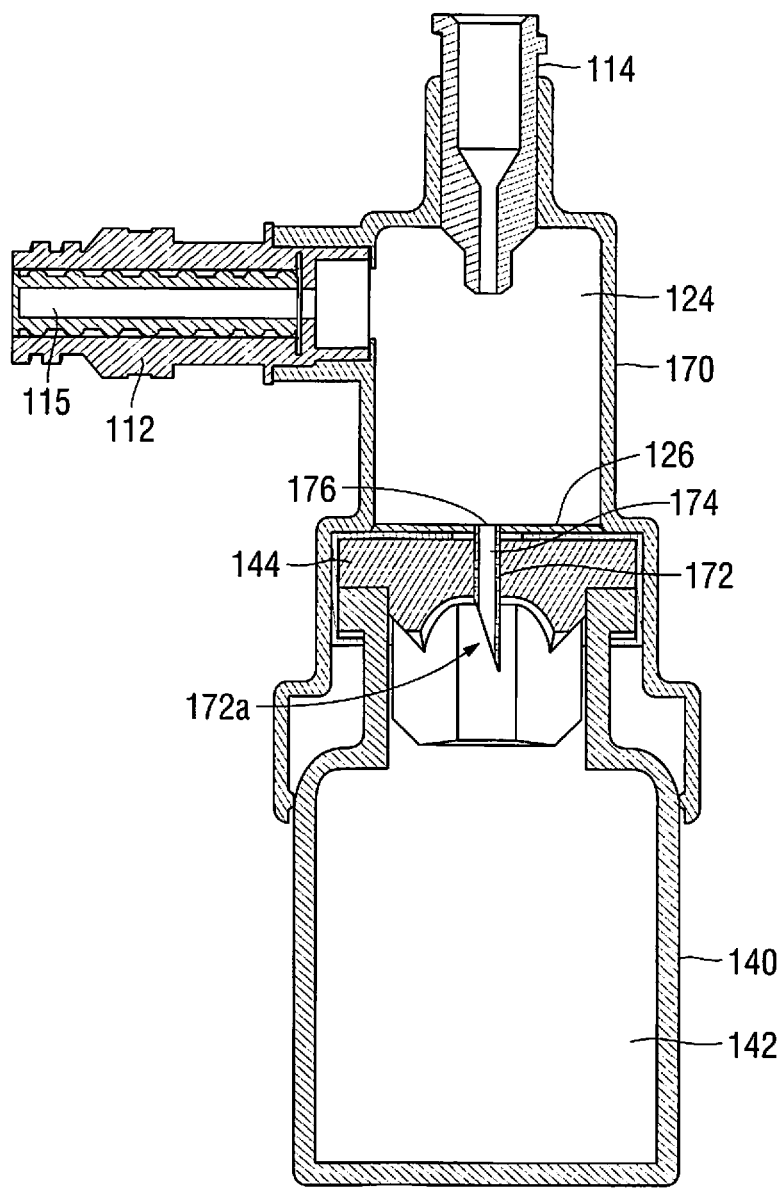
FIG. 15 is a cross-sectional view of an alternate embodiment of the vial adapter attached to a neurotoxin vial of FIG. 13.

In the alternate embodiment of FIG. 15, the adapter 170 is identical to adapter 110 except that the needle 172 does not extend through the chamber 124 as in needle 116 of FIG. 14A. Needle 172 extends from the base 126 through the rubber stopper 144 and into the vial 140. In this version, the saline would be injected into the chamber 124 and the vacuum applied by the chamber 142 of the vial 140 would suction the saline through the needle 172 and into the chamber 142 of the vial 140. To withdraw the reconstituted toxin, the vacuum through side port 112 would draw the toxin through the distal opening 172a in needle 172, through passage 174 and out proximal opening 176 into chamber 124. In all other respects, the feature/components and use of the adapter 170 is identical to adapter 110 so the discussion above for adapter 110 is fully applicable to adapter 170 and like reference numerals are used.

The vial adapter 110 (and other vial adapters disclosed herein) can hold volumes of diluent volumes ranging from less than 1 cc to 4 cc in volume for example, although other volumes are also contemplated. Once a luer locked syringe that is pre-loaded with the desired diluent amount is attached to the vial adapter via the 19 gauge valved port, the adapter is then attached to, e.g., latched onto in some embodiments, a 25 mm vial and that 19 gauge needle gently pierces the rubber stopper of the vacuumed lyophilized vial. The vacuum of the vial draws the diluent from the loaded syringe directly into the vial seamlessly, to the point where all chemically active toxin protein ingredient found within the vial and on its inner walls, in microscopic powder form, is quickly and proficiently reconstituted. In some embodiments, there is no need to shake or swirl the vial in order to ensure proper reconstitution, as the volume of diluent is completely pulled into the vial with a speed and a subsequent torrent that completely bathes the inside of the vial immediately. In essence, no nanoparticle of lyophilized microproduct is left undiluted which produces an ideal, replicable potency of the medicine.

Thus, the vial adapter 110 (and other vial adapters disclosed herein) provides numerous advantages by providing: 1) an easy-to-use, reproducible technique of reconstitution and drawing up neurotoxin using needled-syringe access to the vial; 2) sterility of diluting and drawing up neurotoxin; 3) a filtration system which eliminates the risk of injecting cored pieces of the rubber stopper into a patient's skin, which presents a risk of infection or intravascular obstruction leading to a stroke or blindness; and 4) speeds up the process of getting diluted toxin out of the vial. The vial adapters also decrease medical waste by eliminating the need of using a variety of needles and syringes to dilute and draw up toxin and increase patient satisfaction by eliminating dulling of needled-syringes through the thick rubber stopper which is now standard practice.

The vial adapters of the present invention are preferably disposable—for one time use so it can be provided (i.e., bought/discarded) with each vial.

The vial adapters can include a permanent latching mechanism so that once the adapter is attached to a vial it cannot be removed, so as to be one time use.

The vial adapters can be configured to fit different sized vials so that it can be used beyond the space of neuromodulators and adapt to aspects of cosmetic injectables. The adapter can be utilized for injection of botulinum toxin used for cosmetics such as Botox (sold by Allergan, other brands include Dysport sold by Galderma, Jeaveau sold by Evolus, and Xeomin sold by Merz). Even further, the adapter could be utilized in other fields of medicine, to be integrated into the reconstitution processes of medications such as chemotherapeutics, that also require reconstitution.

Although the apparatus and methods of the subject disclosure have been described with respect to preferred embodiments, those skilled in the art will readily appreciate that changes and modifications may be made thereto without departing from the spirit and scope of the present disclosure as defined by the appended claims.

What is claimed is:

1. A vial adapter for reconstituting a drug and drawing a drug from a vial, the vial adapter comprising
   a) a passageway for passage of a diluent into the vial to mix with and reconstitute the drug; and
   b) a chamber containing the reconstituted drug drawn from the vial;
   c) wherein a vacuum is applied through the adapter to draw the reconstituted drug from the vial into the adapter;
   d) wherein the passageway is formed in a needle extending within the adapter, the needle having a penetrating tip configured to enter the vial and an opening for passage of the diluent into the vial, the needle having a plurality of side openings configured for passage of the reconstituted drug into the chamber via the vacuum, the plurality of side openings configured to remain outside the vial, the chamber formed between an outer wall of the needle and an inner side wall of the adapter, and the plurality of side openings communicating with the chamber.

2. The vial adapter of claim 1, further comprising a first port communicating with the chamber to provide access for a syringe to apply the vacuum to draw the reconstituted drug.

3. The vial adapter of claim 1, wherein the chamber stores the reconstituted drug and the chamber is accessible to withdraw the reconstituted drug therefrom for injection in a patient.

4. The vial adapter of claim 1, further comprising a second port in communication with the passageway, the second port receiving a syringe for inserting the diluent through the adapter and into the vial.

5. The vial adapter of claim 1, wherein the vacuum is applied through the passageway after passage of the diluent.

6. The vial adapter of claim 1, wherein the drug is botulinum toxin.

7. The vial adapter of claim 1, wherein the needle is fixedly attached to the adapter.

8. The vial adapter of claim 1, wherein the vial adapter forms a closed system to maintain the vacuum therein for drawing the reconstituted drug from the vial and the chamber includes an openable opening to selectively break the vacuum.

9. The vial adapter of claim 1, further comprising a filter blocking access of the particles from the vial into the chamber.

10. A vial adapter for drawing a drug from a vial, the vial adapter comprising a) a needle having a passageway and a penetrating tip for accessing an internal chamber of the vial containing the drug, b) a chamber in the adapter positioned proximal of the penetrating tip and external of the passageway of the needle and between an outer wall of the needle and an inner side wall of the adapter, c) a channel at an angular orientation to the chamber and d) a port for injection of saline, the chamber providing access for an injection needle to withdraw the drug from the chamber through the channel and into the injection needle, and a filter separating the chamber to prevent particles from the vial entering into the chamber through the filter.

11. The vial adapter of claim 10, wherein the chamber provides a space for mixing of a dilution liquid with the drug from the vial to reconstitute the drug within the chamber.

12. The vial adapter of claim 10, wherein the needle forms a vacuum for drawing the drug into the chamber.

13. The vial adapter of claim 10, wherein the chamber includes one or both of a) a membrane penetrable by a needled syringe; and b) an access port for a syringe.

14. A method for reconstituting a drug for subsequent injection into a patient, the method comprising the steps of
   a) inserting a penetrating tip of a needle of a vial adapter into a vial containing a drug, the vial adapter connected to the vial;
   b) passing a diluent through a passageway in the adapter for entry into the vial to mix with and reconstitute the drug;
   c) drawing the reconstituted drug from the vial into a chamber of the adapter, the chamber external of a side wall of the needle such that the needle extends along a length of the chamber, and the needle has a plurality of side openings configured for passage of the reconstituted drug from the vial into the chamber via a vacuum;
   d) holding the reconstituted drug in the chamber; and
   e) subsequently withdrawing the reconstituted drug from the chamber.

15. The method of claim 14, wherein the reconstituted drug is drawn from the chamber for injection of the drug into a patient by an injection device.

16. The method of claim 14, wherein the diluent is passed through a passageway in the needle.

* * * * *